United States Patent [19]

Holtshousen

[11] Patent Number: 4,671,957
[45] Date of Patent: Jun. 9, 1987

[54] ANTIBACTERIAL CREAM

[75] Inventor: Peter D. Holtshousen, Florida, South Africa

[73] Assignee: Euroceltique, S.A., Luxembourg

[21] Appl. No.: 806,763

[22] Filed: Dec. 9, 1985

[30] Foreign Application Priority Data

Dec. 12, 1984 [ZA] South Africa .................. 84/9673

[51] Int. Cl.$^4$ .................. A61K 31/79; A61K 33/18
[52] U.S. Cl. ................................ 424/80; 424/150; 514/939; 514/969
[58] Field of Search .............. 424/80, 150; 514/969, 514/939

[56] References Cited

U.S. PATENT DOCUMENTS 4,271,149 6/1981 Winicov et al. ............... 424/150
4,301,145 11/1981 Cestari ........................... 424/80

Primary Examiner—Leonard Schenkman
Attorney, Agent, or Firm—Steinberg & Raskin

[57] ABSTRACT

An antibacterial cream is provided which can be used for topical application in the treatment of burns and other skin disorders. The topical creams of the invention can be used without the need to destroy surface barriers and provide significant penetration into the wound. The creams of the present invention comprise a bacterial agent distributed in a cream base which contains 20–50% of at least one hydrocarbon component and at least one polyol moisturizing component, on a weight to weight basis.

15 Claims, No Drawings

ANTIBACTERIAL CREAM

BACKGROUND OF THE INVENTION

Topical creams containing antibacterial agents, especially iodophors, are effective therapeutics for the treatment of burns and other skin disorders requiring rectification. However, this therapy is limited by the degree of penetration of the active substance through necrotic tissue, pus and other barriers between the surface of the wound and the deep areas of the wound. In these cases, significant therapeutic advantages are gained by using an additional topical preparation (often acidic in nature) to destroy these barriers and allow free penetration of the antibacterial agent deep into the wound.

It is a disadvantage of this method of treatment however, that the application of the additional (acidic) preparation must be highly controlled, since it is the intention to remove surface barriers only and not to penetrate this extra medication deep into the wound itself, where further tissue damage could result from acidic attack.

SUMMARY OF THE INVENTION

It is accordingly a primary object of the present invention to provide new antibacterial creams suitable for topical application to burns and other skin disorders, which creams are effective without the need to use an acidic preparation for the purpose of destroying surface barriers.

It is another object of the present invention to provide topical antibacterial creams which are more effective in the treatment of burns and other skin disorders than can be achieved by the use of the same antibacterial agent in the same amount in other vehicles.

Other objects of the present invention will be apparent from a further reading of the specification and of the appended claims.

According to the present invention, there is provided a topical, antibacterial cream containing an effective quantity of at least one antibacterial agent in a topical cream base, wherein the base comprises 20 to 50 percent (w/w) of a mixture of at least one hydrocarbon component and at least one polyol moisturizing component.

The present cream has a far greater hydrocarbon/moisturizer content than prior art products. It has been surprisingly found that this increased level of hydrocarbon/moisturizer in the cream results in an improved penetration of the antibacterial agent into wound tissue and thereby avoids the need for a preliminary (acidic) treatment and also leads to faster patient recovery.

DETAILED DESCRIPTION OF THE INVENTION

Any of the known antibacterial agents that are at present employed in cream/ointment formulations may be used in the topical, antibacterial creams of this invention. Suitable agents may also possess other therapeutic activities, such as antifungal and antiviral activities.

The preferred antibacterial agents of this invention are, however, the complexes of iodine with organic polymers that are known as iodophors.

Iodophors are water-soluble, physiologically-acceptable complexes of iodine with organic polymers, in which the germicidal and microbiocidal activity of elemental iodine is maintained. Examples of such iodophors include combinations of elemental iodine with detergent polymers, such as nonylphenoxy poly (ethyleneoxy) ethanol and undecoylium chloride. In a particularly preferred embodiment of the present invention, however, the antibacterial agent is a complex of iodine with a non-ionic, non-detergent (non-surface active), water-soluble organic polymer, such as polyvinylpyrrolidone (povidone), polydextrose or a copolymer of sucrose and epichlorohydrin. Of these non-ionic, non-detergent organic polymers, povidone and polydextrose are especially preferred.

Polyvinylpyrrolidone is a non-ionic, non-detergent water soluble, organic polymer that is characterized by an unusual complexing ability, by its colloidal properties and by its physiological inertness. Its iodine complex, polyvinylpyrrolidone-iodine (povidone-iodine), is a well known iodophor that is a highly effective germicide, providing a broad spectrum of microbiocidal action against virtually all microbes.

Povidone-iodine may be prepared by any of a number of known routes, see, for example, European Published Application Nos. 120301A, and 6340A, and GB 1580596.

Polydextrose is a non-nutritive polysaccharide, prepared by the condensation polymerization of saccharides in the presence of polycarboxylic acid catalysts, under reduced pressure. Polydextrose is described in U.S. Pat. Nos. 3,766,105 and 3,786,794, and is available from Pfizer Inc., New York. Commercially available polydextrose polymer is a low molecular weight, water-soluble, randomly bonded polymer of glucose containing minor amounts of sorbitol end groups and citric acid residues attached to the polymer by mono- and di-ester bonds. The numerical average molecular weight of this commercially available material is 1,500, ranging from about 160 to about 20,000.

When polydextrose polymer is combined with elemental iodine, preferably in the presence of an alkali metal iodide, the resultant polydextrose-iodine complex is formed. This complex is a tan-to-amber coloured product which melts between 90° C. and 130° C. to form a red liquid. Polydextrose-iodine powder is highly soluble in water, and at room temperature results in a reddish brown coloured aqueous solution.

The amount of iodine incorporated in the iodophors used in the present cream will be determined by, amongst other factors, the amount of iodophor present in the cream and the required antibacterial strength of the cream. Preferably, iodine will constitute between 1 and 20% (by wt.), more preferably between 2 and 15% (by wt.) of the iodophor dry weight.

The concentration of antibacterial agent in the present cream will depend on the antibacterial strength required. In addition, antibacterial agent concentration will be determined by, amongst other factors, the agent employed, the propensity of the agent to cause irritation and the length of use contemplated. When the antibacterial agent is an iodophor, the concentration will also depend on the amount of iodine in the iodophor and the rate of iodine loss (when the cream is in use).

Thus, when the antibacterial agent is an iodophor, the cream preferably contains enough iodophor to afford a concentration of available (titratable) iodine within the cream of between 0.1% and 2% (by wt.), especially between 0.2 and 1.5% (by wt.).

Thus, a cream employing povidone-iodine, with 10% (by wt.) available iodine, as an antibacterial agent, would preferably contain between 1 and 20%, especially 1 and 15%, (by wt.) of povidone-iodine.

When the antibacterial agent is other than an iodophor the present cream will preferably contain between 0.1 and 2% (by wt.) of the agent.

The topical cream base of the present invention is an oil in water emulsion and must contain between 20 and 50 percent (by wt.) of a mixture of hydrocarbon and polyol moisturizing components. Preferably the cream base contains between 25 and 40 percent (by wt.) of hydrocarbon/moisturizing components.

The hydrocarbon component of the present cream base may be selected from any of the hydrocarbon oils and hydrocarbon bases that are well known in the pharmaceutical art. Suitable hydrocarbon oils are mineral oil or liquid petrolatum, while suitable hydrocarbon bases are white petrolatum or white ointment (petrolatum with 5% beeswax).

In a preferred embodiment of the present invention, the hydrocarbon component comprises between 15 and 40% (w/w), especially between 20-30% (w/w) of the topical cream base.

In a particularly preferred embodiment of the present invention, the hydrocarbon component comprises a mixture of liquid petrolatum and white petrolatum.

The polyol moisturizing component of the present cream base may be selected from any of the polyol moisturizing components that are well known in the pharmaceutical art.

Examples include propylene glycol. Most preferred is glycerin.

In a preferred embodiment of the present invention, the polyol moisturizing component comprises between 5 and 20% (w/w), especially between 5 and 15% (w/w) of the topical cream base.

Although any ratio of hydrocarbon to polyol components that produces a satisfactory cream for topical application may be employed in the present cream base, it has been found according to the present invention that ratios (w/w) between 1 to 1 and 4 to 1, especially a weight ratio of about 2 to 1, provide the most satisfactory cream bases for incorporation in the present topical cream.

In addition to hydrocarbon and polyol moisturizing components, the present cream base will generally also contain at least one emulsifier, and, optionally, but preferably, at least one surfactant.

Suitable emulsifiers include higher fatty alcohols, such as cetyl alcohol, stearyl alcohol, and cetostearyl alcohol, and partially esterified polyols such as glyceryl monostearate, polyethylene glycol monostearate and sorbitan monooleate.

Preferably emulsifiers are provided at a concentration between 1 and 15% (by wt.) of the cream base.

The present antibacterial cream must be of a viscosity that allows its topical application to the human or animal body. Preferably the cream will have a viscosity at 25° C. between 25,000 and 67,000 centipoises, when measured on a Brookfield (Trade Mark) LV Viscometer, most preferably between 30,000 and 50,000 centipoises.

In order to facilitate the preparation of the present cream there is provided, in a further aspect of the present invention, a process for the preparation of a topical, antibacterial cream comprising forming a mixture of an effective quantity of at least one antibacterial agent and a topical cream base, wherein the base comprises 20 to 50% (w/w) of a mixture of at least one hydrocarbon component and at least one polyol moisturizing component. In one embodiment of the present process, the cream is prepared by forming an aqueous solution containing at least one antibacterial agent and at least one polyol moisturizing component and then mixing this aqueous solution with the at least one hydrocarbon component. In another, preferred, embodiment of the present process, the cream is prepared by forming an aqueous solution of at least one polyol moisturizing component, mixing the aqueous polyol solution with at least one hydrocarbon component to form a base and adding an aqueous solution of the antibacterial agent to the base. In either case, further components, e.g. emulsifiers, may be distributed in either the aqueous or the hydrocarbon phase, as desired.

In order to treat, for example, burns and other skin disorders, the present cream may be applied to the human or animal body by any of the conventional methods known in the medical pharmaceutical art. For example, the cream may first be applied to a suitable dressing, such as a Teflon dressing, which is then placed on the wound tissue. The dressing may be held in place by a bandage. Generally, the dressing will be replaced every 12 to 24 hours. The cream may be applied alone or, although this is not necessary for successful treatment, in combination with a known acid cream, for example a benzoic acid containing cream, such as Aserbine (Trade Mark).

Clinical trials using a povidone-iodine cream according to the present invention have shown that the cream affords an improved penetration of the povidone-iodine into wounds and that the cream has a superior therapeutic profile, when compared with known povidone-iodine products (especially ointments) of the prior art which contain a low content of hydrocarbon and moisturizing components. In particular, the present cream has an improved (i.e. shorter) recovery than these prior art products and does not require the use of other agents, as do the prior art products.

DESCRIPTION OF PREFERRED EMBODIMENTS

Materials (i) Polydextrose-Iodine (4% concentration)

Deionized water (31.2g) was placed in a stainless steel vessel fitted with an efficient mixer. With vigorous stirring, polydextrose (46.0 g., Pfizer, Chemical Division, NY) was slowly added (in a portionwise manner). Once the polydextrose was dissolved in the water, potassium iodide (18.6 g., USP) was added and the vigorous stirring was continued. The potassium iodide was allowed to dissolve to give a clear solution and then iodine (4.29 g. USP) was slowly added, once again with vigorous stirring. The stirring was continued until the amount of titratable iodine present, in samples taken from the reaction mixture, remained constant over a period of one hour. Finally the reaction mixture was filtered through a 200 mesh stainless steel rigimesh filter. The final solution was opaque and red-brown in colour. The polydextrose-iodine complex in the solution had an available (titrable) iodine content of about 4% (w/w).

(ii) Polydextrose-Iodine (7% available iodine)

The procedure of Example (i) was followed except that the proportions of the components were adjusted to give a polydextrose-iodine solution having an available iodine content of about 7% (w/w).

(iii) Povidone-Iodine

Povidone-Iodine (PVPI) may be obtained from either BASF AG, D-6700 Ludwigshafen, West Germany or GAF Corp., Wayne, N.J. 07470, USA.

EXAMPLE 1

A topical antibacterial cream having the following ingredients

|  | wt. % |
|---|---|
| Povidone-Iodine USP | 5 (15% overage) |
| Stearyl Alcohol NF | 2 |
| Cetyl Alcohol NF | 2 |
| White Petrolatum USP | 7.5 |
| Liquid Petrolatum USP | 14.5 |
| Glycerin USP | 12 |
| Polysorbate 60 NF | 1 |
| Polyoxyethylene Stearate (Myrj 53) | 1.3 |
| Sorbitan Monostearate (Arlacel 60) | 0.7 |
| Sodium Hydroxide | 0.1 |
| Purified Water | qs to 100% | was prepared as follows

The stearyl alcohol, cetyl alcohol, white petrolatum, liquid petrolatum, sorbitan monostearate and polyoxyethylene stearate were melted with mixing. Separately, PVPI was dissolved in water, after which the pH of the solution was adjusted to about 4.5 using NaOH.

An aqueous solution of polysorbate 60 and glycerine was then heated and added to the melt, with stirring, to form an emulsion. To the emulsion was added the PVPI solution, the whole being stirred until the batch reached room temperature. (During the final stage, water and/or hydroxide base may be added to the batch, as required). The resulting cream had a viscosity of 40,000 centipoises at 25° C., measured on a Brookfield LV viscometer.

EXAMPLE 2

A topical, antibacterial cream having the following ingredients was prepared as described in Example 1:

|  | wt. % |
|---|---|
| Povidone-Iodine USP | 5 (15% overage) |
| Stearyl Alcohol NF | 2 |
| Cetyl Alcohol NF | 2 |
| White Petrolatum USP | 12 |
| Liquid Petrolatum USP | 10 |
| Glycerin USP | 8 |
| Polysorbate 60 NF | 2 |
| PEG Monostearate | 1 |
| Sodium Hydroxide | 0.1 |
| Purified Water | qs to 100 |

EXAMPLE 3

A cream according to Example 1 was prepared except that the povidone-iodine was replaced by polydextrose-iodine, 12.5% (by wt.) of 4% concentration

EXAMPLE 4

A cream according to Example 1 was prepared except that the povidone-iodine was replaced by polydextrose-iodine, 7% (by wt.) of 7% concentration.

Clinical Trial

Topical burn therapy comparing providone-iodine ointment or cream plus aserbine and povidone-iodine cream of the present invention Materials (a) 10% povidone-iodine (Betadine, Trade Mark) ointment was obtained from Napp Laboratories, cambridge, England.

(b) 5% povidone-iodine cream was prepared as described in Example 1

(c) Aserbine (Trade Mark) cream containing benzoic acid (0.025%, malic acid (0.375%), salicylic acid (0.006%), propylene glycol and hexachlorophane, was obtained from Bencard, UK.

Methods

Three groups, each consisting of 25 patients, were treated by topical application, on a once daily basis, of (i) 10% Betadine ointment mixed in equal proportions with Aserbine cream, or (ii) 5% Povidone-iodine cream, or (iii) 5% Povidone-iodine cream mixed in equal proportions with Aserbine cream.

The daily application of fresh topical agent was preceded by wound cleansing in a whirlpool tank. Control of bacterial proliferation in the water and pump was achieved by adding PVPI to the water in a concentration of 3 ppm. (This concentration has been shown to be effective in preventing bacterial proliferation and cross-contamination in hydrotherapy equipment).

Systemic antibiotics were not employed except in those patients manifesting signs and symptoms of invasive infection.

The groups were comparable for age, size, type, depth and distribution of burn.

Results

All three preparations were applied easily and removed easily causing only mild discomfort on application in the majority of cases. Moderate discomfort on application was experienced by a few patients but was never severe enough to necessitate the use of analgesic agents. In no instance was it necessary to discontinue treatment because of discomfort. Results are shown in the Tables.

TABLE 1

Superficial Wound Healing

| | Therapy (no. of days) | | |
|---|---|---|---|
| Percentage of burn (%) | PVPI Ointment Plus Aserbine | PVPI Cream | PVPI Cream plus Aserbine |
| 0.10 | 8 | 11 | 6 |
| 10–20 | 13.5 | 15 | 13 |
| 20–30 | 36.5 | 25 | 20 |

TABLE II

Deep Wound Healing

| | Therapy (no. of days) | | |
|---|---|---|---|
| Percentage of burn (%) | PVPI Ointment Plus Aserbine | PVPI Cream | PVPI Cream plus Aserbine |
| 0.10 | 23 | 28 | 11 |
| 10–20 | 25 | 24 | 24 |
| 20–30 | 39 | 28 | 32 |
| 30–40 | — | 30 | — |
| 40–50 | — | 33 | 34 |
| 50–60 | — | — | — |
| 60–70 | — | — | — |
| 70–80 | 72 | — | — |

TABLE III

| Organism | PVPI Ointment plus Aserbine | PVPI Cream | PVPI Cream plus Aserbine |
|---|---|---|---|
| *Staphylococcus aureus* | 56 | 17 | 10 |
| *Pseudomonas aeruginosa* | 19 | 6 | 7 |
| Streptococcus spp. | 5 | 4 | 3 |
| *Escherichia coli* | 1 | — | 1 |
| *Proteus mirabilis* | 1 | 4 | — |
| *Acetinobacter anitratus* | 1 | 1 | 2 |
| *Enterobacter cloacae* | — | 1 | 1 |
| *Serratia marcescens* | — | — | 1 |
| Total | 83 | 33 | 25 |

Bacteriology: Therapy (no. of isolates)

Healing Times

Differences were observed in healing times. Superficial burns of between 20 and 30% total body surface area healed within 20–25 days when treated with PVPI cream with or without Aserbine, as opposed to an average of 36.5 days when treated with PVPI ointment plus Aserbine. Similar improved healing times were also seen in deep burns treated with the cream as opposed to those treated with the ointment plus Aserbine. Deep burns of between 40 and 50% total body surface area treated with the cream healed significantly faster than those burns of 20 to 30% total body surface area treated with the ointment plus Aserbine.

In all of the above cases, it is important to note that the present cream which contains half as much PVPI as the ointment had significantly faster healing times.

Bacteriology

A decrease in positive bacterial cultures was observed for *S. aureus* and *P. aeruginosa* in burns treated with PVPI cream with or without Aserbine as opposed to those treated with the ointment plus Aserbine.

Complications

Apart from two patients who developed septicaemia, which responded to systemic administration of tobramycin, no other serious complications were observed.

A Comparison of the Killing Times of a PVPI Cream and A PVPI Ointment Against Staphylococcus Aureus Materials (i) PVPI Ointment (Betadine, trade mark, ointment) available from K4Napp Laboratories, Cambridge.

(ii) PVPI Cream, prepared in accordance with Example 2 above.

Medium

Trypticase soy bean case in

Digest Broth (TSB) and Agar (TSA)

Test Organisms

*staphylococcus aureus* ATCC 6538

Method

Determination of Killing Time (KT)

A stock culture of the test organism was maintained on TSA slants and was transferred to TSB 24 hours prior to the test. 0.2 ml. of the TSB culture was added to 5 g. of each agent. After mixing, a 4 mm loopful of the mixture was removed at intervals and was transferred to 10 ml. of TSB. Following incubation for 48 hrs. at 33° C., all cultures were examined for growth. Organism viability and carry over controls were carried out and were positive for growth for each agent.

Two of the above tests were carried out. Results are shown in the Tables.

TABLE IV

Killing Times of two PVPI formulations Against *S. aureus* First Test

| Agent | 1 | 2 | 3 | 4 | 5 | 7 | 10 | 12 | 15 | 30 | 35 | 40 | 45 | 60 |
|---|---|---|---|---|---|---|---|---|---|---|---|---|---|---|
| PVPI Ointment | + | + | + | + | + | + | + | + | + | + | + | − | − | − |
| PVPI Cream | + | + | − | − | − | − | − | − | − | − | − | − | − | − |

Times (Minutes)

TABLE V

Killing Times of two PVPI Formulations Against *S. aureus* Second Test

| Agent | 1 | 2 | 3 | 4 | 5 | 7 | 10 | 12 | 15 | 30 | 35 | 40 | 45 | 60 |
|---|---|---|---|---|---|---|---|---|---|---|---|---|---|---|
| PVPI Ointment | + | + | + | + | + | + | + | + | + | + | − | − | − | − |
| PVPI Cream | + | + | − | − | − | − | − | − | − | − | − | − | − | − |

Times (Minutes)

While the invention has been described in particular with respect to certain specific antibacterial agents, it is apparent that variations and modifications of the invention can be made without departing from the spirit or scope thereof.

What is claimed is:

1. Antibacterial cream for topical application, said cream comprising an antibacterial effective amount of polyvinyl-pyrrolidone-iodine distributed in an oil-in-water emulsion topical cream base containing water and, in an amount of 20–50% by weight, a mixture of at least one hydrocarbon component, and at least one polyol moisturizing component, wherein about 15–40% by weight of said base is comprised of said hydrocarbon component, and
    about 5–20% by weight of said base is comprised of said polyol moisturizing component.

2. Antibacterial cream according to claim 1 wherein said base contains 25–40% of said mixture.

3. Antibacterial cream according to claim 1 wherein said hydrocarbon component is selected from the group consisting of mineral oil, liquid petrolatum, white petrolatum and white ointment.

4. Antibacterial cream according to claim 1 wherein said hydrocarbon component is a mixture of liquid petrolatum and white petrolatum.

5. Antibacterial cream according to claim 1 wherein the hydrocarbon component of said base constitutes 20–30% by weight thereof.

6. Antibacterial cream according to claim 1 wherein said polyol moisturizing component is glycerin.

7. Antibacterial cream according to claim 1 wherein said polyol moisturizing component constitutes 5–15% by weight of said base.

8. Antibacterial cream according to claim 1 wherein the ratio by weight of said hydrocarbon component to said polyol moisturizing component is between 1:1 and 4:1.

9. Antibacterial cream according to claim 8 wherein the ratio by weight of said hydrocarbon component to said polyol moisturizing component is about 2:1.

10. Antibacterial cream according to claim 1 and also including at least one emulsifier.

11. Antibacterial cream according to claim 10 wherein the amount of said emulsifier is about 1–15% by weight of said base.

12. Antibacterial cream according to claim 1 and having a viscosity adjusted to between about 25,000 and 67,000 centipoises at 25° C.

13. Antibacterial cream according to claim 1 wherein said iodophor is present in an amount to provide an available iodine concentration of about 0.1–2% by weight.

14. Antibacterial cream according to claim 13 wherein the amount of available iodine is about 0.2–1.5% by weight.

15. Method of treating burns and other skin disorders, which comprises applying topically to an area of the skin requiring such treatment, an antibacterial cream containing an antibacterial effective amount of polyvinylpyrrolidone-iodine distributed in an oil-in-water emulsion topical cream base containing water and, in an amount of 20–50% by weight, a mixture of at least one hydrocarbon component, and at least on polyol moisturizing component.

wherein about 15–40% by weight of said base is comprised of said hydrocarbon component, and about 5–20% by weight of said base is comprised of said polyol moisturizing component.

* * * * *